United States Patent [19]

Ojima et al.

[11] Patent Number: 4,581,452

[45] Date of Patent: Apr. 8, 1986

[54] PRODUCTION OF 5-PERFLUOROALKYLDIHYDROURACIL DERIVATIVES

[75] Inventors: Iwao Ojima; Takamasa Fuchikami; Makoto Fujita, all of Sagamihara, Japan

[73] Assignee: Sagami Chemical Research Center, Tokyo, Japan

[21] Appl. No.: 526,880

[22] Filed: Aug. 26, 1983

[30] Foreign Application Priority Data

Aug. 31, 1982 [JP] Japan ................. 57-150075

[51] Int. Cl.$^4$ .................. C07D 239/22; C07C 57/03; C07C 125/17; C07C 157/05
[52] U.S. Cl. .................. 544/309; 562/553; 562/556; 562/560; 564/31; 564/58; 564/60
[58] Field of Search ............... 544/309; 562/556, 560; 564/31, 58, 60

[56] References Cited

U.S. PATENT DOCUMENTS 2,572,568 10/1951 Gluesenkamp ............... 562/560
3,201,387 8/1965 Heidelberger ............... 544/309

OTHER PUBLICATIONS

Heidelberger et al., J. Med. Chem., vol. 7, No. 1, pp. 1–5, (1964).

*Primary Examiner*—Donald G. Daus
*Assistant Examiner*—Stephen M. Kapner
*Attorney, Agent, or Firm*—Wenderoth, Lind & Ponack

[57] ABSTRACT

A process for preparing a 5-perfluoroalkyl-dihydrouracil derivative of the general formula

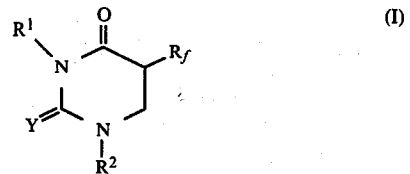

wherein $R_f$ represents a perfluoroalkyl group, each of $R^1$ and $R^2$ represents a hydrogen atom, or an alkyl, cycloalkyl, aryl, aralkyl or heterocyclic group, and Y is an oxygen or sulfur atom, which comprises (a) reacting a compound of the general formula

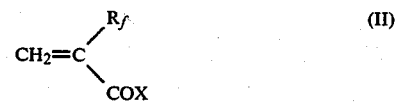

wherein X represents a halogen atom or hydroxyl group, with a urea derivative of the general formula

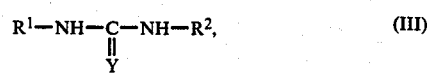

provided that when X is a hydroxyl group and at least one of $R^1$ and $R^2$ is a hydrogen atom, said reaction is carried out in the presence of a condensing agent, or (b) cyclizing a compound of the general formula

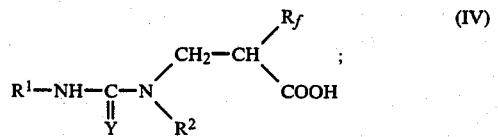

and a novel intermediate compound of the above formula (IV).

12 Claims, No Drawings

PRODUCTION OF 5-PERFLUOROALKYLDIHYDROURACIL DERIVATIVES

This invention relates to the production of 5-perfluoroalkyldihydrouracil derivatives. More specifically, it relates to a process for preparing 5-perfluoroalkyl-5,6-dehydrouracil derivatives of the following formula

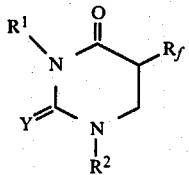

wherein $R_f$ represents a perfluoroalkyl group, each of $R^1$ and $R^2$ represents a hydrogen atom or an alkyl, cycloalkyl, aryl, aralkyl or heterocyclic group, and Y is an oxygen or sulfur atom; and to novel intermediate compounds useful for this process.

Among the 5-perfluoroalkyldihydrouracils of formula (I), 5-trifluoromethyldihydrouracil is a known compound which can be converted to trifluorothymine by reacting it with bromine in acetic acid followed by heating [C. Heidelberger, D. G. Parsons and D. C. Remy, J. Med. Chem., 7, 1(1964)]. Condensation of trifluorothymine with a sugar can yield trifluorothymidine or its derivative which has anticancer and antiviral activities and is useful as a drug for treating ceratitis and herpes. The compounds of formula (I) other than 5-trifluoromethyldihydrouracil are novel compounds which are not described in the prior literature. They have antitumor activity against ascitic mastocarcinoma and are expected to be useful as an anticancer agent.

One conventional method for synthesizing 5-trifluoromethyldihydrouracil comprises converting trifluoroacetone to cyanohydrin, acetylating the product, heat-decomposing the acetylated product, reacting the resulting alpha-trifluoroacrylonitrile with hydrogen bromide in methanol to form beta-bromo-alpha-trifluoromethylpropionamide, reacting the amide with urea or acetylurea, and cyclizing the resulting compound in hydrochloric acid [C. Heidelberger, D. G. Parsons and D. C. Remy, J. Med. Chem., 7, 1 (1964)].

The above conventional method includes many steps, and the total yield attained is as low as 7 to 16%. It has never proved to be commercially satisfactory.

It is an object of this invention to provide a novel and commercial process for producing the 5-perfluoroalkyldihydrouracil derivatives of general formula (I) above.

Another object of this invention is to provide novel intermediate compounds which are useful for the above manufacturing process.

Other objects and advantages of this invention will become apparent from the following detailed description.

According to the present invention, the 5-perfluoroalkyldihydrouracil derivatives of formula (I) are prepared by a process which comprises (a) reacting a compound of the general formula

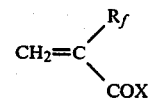

wherein X represents a halogen atom or a hydroxyl group and $R_f$ is as defined above,
with a urea derivative of the general formula

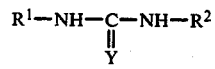

wherein $R^1$, $R^2$ and Y are as defined above, provided that when X is a hydroxyl, group and at least one of $R^1$ and $R^2$ is a hydrogen atom, said reaction is carried out in the presence of a condensing agent, or (b) cyclizing a compound of the general formula

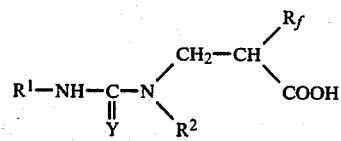

wherein $R_f$, $R^1$, $R^2$ and Y are as defined above.

In formulae (I), (II) and (IV), the "perfluoroalkyl group" represented by $R_f$ is a group resulting from substitution of fluorine atoms for all of the hydrogen atoms bonded to the carbon atom or atoms of an alkyl group, and may be linear or branched. It may contain 1 to 20, preferably 1 to 5, carbon atoms. Examples of the perfluoroalkyl group include trifluoromethyl, pentafluoroethyl, n-heptafluoropropyl, heptafluoro-isopropyl, nonafluorobutyl, nonafluoro-isobutyl, nonafluoro-sec-butyl, nonafluoro-tert-butyl, perfluoropentyl, perfluoroheptyl and perfluorooctyl. Lower perfluoroalkyl groups, particularly trifluoromethyl, are preferred.

In the present specification, the term "lower" is used to show that a compound or group qualified by this term has not more than 5 carbon atoms.

The "alkyl group" represented by $R^1$ and/or $R^2$ in formula (III) may be linear or branched, and includes, for example, methyl, ethyl, propyl, isopropyl, butyl, isobutyl, sec-butyl, tert-butyl, pentyl, isoamyl, hexyl, heptyl, octyl, 2-ethylhexyl and decyl. Preferably, these alkyl groups contain up to 10 carbon atoms, and more preferably they are lower alkyl groups. The "cycloalkyl group" may generally contain 3 to 10 carbon atoms, and may further contain a lower alkyl group such as methyl on the ring. Examples include cyclopropyl, cyclobutyl, cyclopentyl, cyclohexyl, methylcyclohexyl, cycloheptyl, cyclooctyl and cyclo[4.4.0]decyl. The "aryl group" includes, for example, phenyl, tolyl, xylyl and naphthyl, and a phenyl group is preferred. The "aralkyl group" is an aryl-substituted alkyl group in which the alkyl and aryl have the aforesaid meanings. Examples include benzyl, alpha-phenethyl and beta-phenethyl. Benzyl is preferred. The "heterocyclic group" includes 5- or 6-membered heterocyclic groups such as tetrahydrofuryl, furyl, 2-oxo-3-tetrahydrofuryl, 2,3,4,6-tetra-O-acetyl-beta-D-glucopyranosyl or 3,5-di-O-benzoyl-deoxy-beta-D-2-ribofuranosyl.

In embodiment (a) of the process of this invention, the alpha-perfluoroalkylacrylic acid or its halide of formula (II) is reacted with the (thio)urea derivative of formula (III).

This reaction can be carried out in the absence of solvent. Usually, however, it is performed in a solvent which does not participate in the reaction. For example, there can be used ether solvents such as tetrahydrofuran, dibutyl ether, dioxane, dimethoxyethane and diglyme, hydrocarbon solvents such as benzene, toluene and xylene, aprotic polar solvents such as dimethylformamide (DMF), dimethylsulfoxide (DMSO), 1,3-dimethyl-2-imidazolidinone, hexamethylphosphonamide and acetonitrile. Of these, aprotic polar solvents are preferred.

When a compound of formula (II) in which X represents a hydroxyl group and a compound of formula (III) in which at least one of $R^1$ and $R^2$ is a hydrogen atom are used as the starting materials, this reaction is carried out in the presence of a condensing agent. Even in the absence of a condensing agent, the desired compound of formula (I) may sometimes be formed in a very low yield as seen, for example, in Example 9 given hereinbelow. The presence of a condensing agent, however, can always lead to high yields of the desired compound of formula (I). Examples of the condensing agent which can be used in this invention include dicyclohexylcarbodiimide (DCC), polyphosphoric acid, p-toluenesulfonic acid and carboxylic acid anhydrides of the formula $(R^3CO)_2O$ (wherein $R^3$ represents a hydrogen atom, a lower alkyl group, a lower haloalkyl group or an aryl group, or the two $R^3$'s may together form a lower alkylene group) such as formic anhydride, acetic anhydride, propionic anhydride, trifluoroacetic anhydride, benzoic anhydride, succinic anhydride, glutaric anhydride, and adipic anhydride.

Of these condensing agents, DCC and carboxylic acid anhydrides, particularly acetic anhydride, are preferred. The amount of the condensing agent used is not critical. Generally, it is 1 to 10 moles per mole of the compound of formula (I). The carboxylic acid anhydride may be used in large excess to cause it to serve also as a solvent.

When a compound of formula (II) in which X is a halogen atom is used, and particularly when the (thio)urea derivative of formula (III) having a functional substituent sensitive to hydrogen halide generated during the reaction is used, the above reaction is carried out optionally in the presence of an acid-trapping agent. Examples of acid-trapping agents that can be used for this purpose include tertiary amines such as triethylamine, pyridine and N-methylmorpholine, and alkalies such as sodium hydrogen carbonate, sodium carbonate, sodium hydroxide and potassium hydroxide. The amount of the acid-trapping agent used is not critical. Its suitable amount is generally 1 to 5, preferably 1 to 1.2, equivalents, per mole of the compound of formula (II).

The temperature at which the above reaction is carried out is not strictly limited, and can be varied depending upon the types of the starting materials, etc. Generally, it is about −50° C. to the refluxing temperature of the reaction mixture, preferably about −20° C. to about 120° C. The more preferred reaction temperature may be selected suitably according to the starting compound of formula (II) used. For example, when compound of formula (II) in which X is a halogen atom is used, relatively low reaction temperatures of about −20° C. to about 50° C. are advantageously used. When a compound of formula (II) in which X represents a hydroxyl group is to be reacted with a compound of formula (III) in which at least one of $R^1$ and $R^2$ represents a hydrogen atom in the presence of the aforesaid condensing agent, reaction temperatures in the range of about −20° C. to about 120° C. are preferred. In the reaction of a compound of formula (II) in which X represents a hydroxyl group with a compound of formula (III) in which $R^1$ and $R^2$ both represent substituents other than a hydrogen atom, relatively elevated temperatures of about 50° C. to about 200° C., especially about 80° C. to about 120° C., are conveniently used.

The amount of the compound of formula (III) relative to the compound of formula (II) is not critical, and can be varied depending upon the types of the starting materials used, etc. Generally, a suitable amount is 0.5 to 2 moles per mole of the compound of formula (II).

The alpha-perfluoroalkylacrylic acid or its halide of formula (II) used as a starting material in the above reaction can be obtained, for example, by reacting an α-halo-α-perfluoroalkylethylene, carbon monoxide and water and as required, halogenating the reaction product. For specific reaction conditions for this reaction, reference may be had to Referential Examples 1 to 3 given hereinbelow. Examples of the compound of formula (II) include alpha-trifluoromethylacrylic acid, alpha-pentafluoroethylacrylic acid, alpha-heptafluoropropylacrylic acid, alpha-heptafluoro-isopropylacrylic acid, alpha-nonafluorobutylacrylic acid, alpha-nonafluoro-isobutylacrylic acid, alpha-nonafluoro-sec-butylacrylic acid, alpha-nonafluoro-tert-butylacrylic acid, alpha-perfluoropentylacrylic acid, alpha-perfluoroheptylacrylic acid, alpha-perfluorooctylacrylic acid, and the corresponding halides such as the chlorides and bromides thereof.

The (thio)urea derivatives of formula (III) to be reacted with the compounds of formula (II) are known compounds or can be produced in accordance with the methods of production of the known compounds. Examples include urea, methylurea, ethylurea, cyclohexylurea, phenylurea, benzylurea, 2-tetrahydrofurylurea, 1,3-dimethylurea, 1,3-diphenylurea, 1,3-dibenzylurea, 1-methyl-3-(2-tetrahydrofuryl)urea, and the corresponding thiourea derivatives.

In embodiment (b) of the process in accordance with this invention, the compound of formula (IV) is cyclized.

The cyclization reaction can be carried out in the absence of a solvent. Usually, however, it is carried out in a solvent which does not participate in the reaction. Examples of the solvent are ether solvents such as tetrahydrofuran, dibutyl ether, dioxane, dimethoxyethane and diglyme, hydrocarbon solvents such as benzene, toluene and xylene, aprotic polar solvents such as dimethylformamide, dimethyl sulfoxide, 1,3-dimethyl-2-imidazolidinone, hexamethylphosphonamide and acetonitrile.

The cyclization may be carried out in the presence of the same condensing agent as described above, preferably dicyclohexylcarbodiimide (DCC) and acetic anhydride. The amount of the condensing agent is not critical. Advantageously, it is used generally in an amount of 1 to 1.2 moles per mole of the compound of formula (IV). When the condensing agent is a carboxylic acid anhydride, it may be used in large excess to cause it to serve also as a solvent.

The cyclization reaction temperature is also not critical, and can be varied widely depending upon the types of the compound of formula (IV) and the condensing agent, etc. The temperature is generally about $-20°$ C. to about 200° C., preferably about 0° C. to about 120° C.

The compound of formula (IV) used as a starting material in this reaction is a novel compound not described in the prior literature, and can be produced by the addition-reaction of a (thio)urea derivative of the following formula

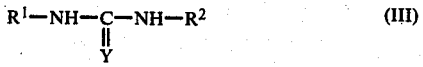   (III)

wherein $R^1$, $R^2$ and Y are as defined above, with an alpha-perfluoroalkylacrylic acid of the following formula

   (II-1)

wherein $R_f$ is as defined hereinabove.

The above addition-reaction can be carried out in a solvent of the types exemplified hereinabove with regard to the reaction of the compound of formula (II) with the compund of formula (III). The reaction can be advantageously carried out under heating conditions generally at a temperature of from about 50° C. to the refluxing temperature of the reaction mixture, preferably from about 80° C. to about 150° C.

The amount of the compound of formula (III) relative to the compound of formula (II-1) is not critical. A suitable amount of the compound of formula (III) is generally 0.5 to 10 moles, preferably 1 to 2 moles, per mole of the compound of formula (II-1).

The compound of formula (IV) can be isolated from the reaction mixture and purified by methods known per se such as chromatography, recrystallization, or distillation. But without isolating it, its cyclization may be carried out successively to the addition-reaction as a one-pot process, and this is preferred.

Typical examples of the compound of formula (IV) are given below.

(2-hydroxycarbonyl-3,3,3-trifluoropropyl)urea,
(2-hydroxycarbonyl-3,3,3-trifluoropropyl)thiourea,
1-methyl-3-(2-hydroxycarbonyl-3,3,3-trifluoropropyl)urea,
1-methyl-3-(2-hydroxycarbonyl-3,3,3-trifluoropropyl)thiourea,
1,3-dimethyl-3-(2-hydroxycarbonyl-3,3,3-trifluoropropyl)urea,
1,3-dimethyl-3-(2-hydroxycarbonyl-3,3,3-trifluoropropyl)thiourea,
1-ethyl-3-(2-hydroxycarbonyl-3,3,3-trifluoropropyl)urea,
1-ethyl-3-(2-hydroxycarbonyl-3,3,3-trifluoropropyl)thiourea,
1-phenyl-3-(2-hydroxycarbonyl-3,3,3-trifluoropropyl)urea,
1-phenyl-3-(2-hydroxycarbonyl-3,3,3-trifluoropropyl)thiourea,
1,3-phenyl-3-(2-hydroxycarbonyl-3,3,3-trifluoropropyl)urea,
1,3-phenyl-3-(2-hydroxycarbonyl-3,3,3-trifluoropropyl)thiourea,
1-phenyl-3-methyl-3-(2-hydroxycarbonyl-3,3,3-trifluoropropyl)urea,
1-phenyl-3-methyl-3-(2-hydroxycarbonyl-3,3,3-trifluoropropyl)thiourea,
1-benzyl-3-(2-hydroxycarbonyl-3,3,3-trifluoropropyl)urea,
1-benzyl-3-(2-hydroxycarbonyl-3,3,3-trifluoropropyl)thiourea,
1-methyl-1-(2-hydroxycarbonyl-3,3,3-trifluoropropyl)urea,
1-methyl-1-(2-hydroxycarbonyl-3,3,3-trifluoropropyl)thiourea,
1-tetrahydrofuryl-3-(2-hydroxycarbonyl-3,3,3-trifluoropropyl)urea,
1-tetrahydrofuryl-3-(2-hydroxycarbonyl-3,3,3-trifluoropropyl)thiourea,
1-methyl-3-(2-hydroxycarbonyl-3,3,4,4,4-pentafluorobutyl)urea,
1-methyl-3-(2-hydroxycarbonyl-3,3,4,4,4-pentafluorobutyl)thiourea,
1-benzyl-3-(2-hydroxycarbonyl-3,3,4,4,4-pentafluorobutyl)urea,
1-benzyl-3-(2-hydroxycarbonyl-3,3,4,4,4-pentafluorobutyl)thiourea,
1-methyl-3-(2-hydroxycarbonyl-3,3,4,4,5,5,5-heptafluoropentyl)urea,
1-methyl-3-(2-hydroxycarbonyl-3,3,4,4,5,5,5-heptafluoropentyl)thiourea,
1-benzyl-3-(2-hydroxycarbonyl-3,3,4,4,5,5,5-heptafluoropentyl)urea,
1-benzyl-3-(2-hydroxycarbonyl-3,3,4,4,5,5,5-heptafluoropentyl)thiourea,
1-methyl-3-(2-hydroxycarbonyl-3,3,4,4,5,5,6,6,6-nonafluorohexyl)urea,
1-methyl-3-(2-hydroxycarbonyl-3,3,4,4,5,5,6,6,6-nonafluorohexyl)thiourea,
1-benzyl-3-(2-hydroxycarbonyl-3,3,4,4,5,5,6,6,6-nonafluorohexyl)urea,
1-benzyl-3-(2-hydroxycarbonyl-3,3,4,4,5,5,6,6,6-nonafluorohexyl)thiourea,
1-methyl-3-(2-hydroxycarbonyl-2-perfluorooctylethyl)urea,
1-methyl-3-(2-hydroxycarbonyl-2-perfluorooctylethyl)thiourea,
1-benzyl-3-(2-hydroxycarbonyl-2-perfluorooctylethyl)urea,
1-benzyl-3-(2-hydroxycarbonyl-2-perfluorooctylethyl)thiourea,
1-methyl-3-(2-hydroxycarbonyl-2-perfluoro-isopropylethyl)urea,
1-methyl-3-(2-hydroxycarbonyl-2-perfluoro-isopropylethyl)thiourea,
1-benzyl-3-(2-hydroxycarbonyl-2-perfluoro-isopropylethyl)urea,
1-benzyl-3-(2-hydroxycarbonyl-2-perfluoro-isopropylethyl)thiourea,
1-furyl-3-(2-hydroxycarbonyl-3,3,3-trifluoropropyl)urea,
1-(2,3,4,6-tetra-O-acetyl-$\beta$-D-glucopyranosyl)-3-(2-hydroxylcarbonyl-3,3,3-trifluoropropyl)thiourea, and
1-(3,5-di-O-benzoyl-2-deoxyl-$\beta$-D-ribofuranosyl)-3-(2-hydroxycarbonyl-3,3,3-trifluoropropyl)urea.

The compound of formula (I) produced by embodiment (a) or (b) can be isolated from the reaction mixture, and purified, by methods known per se such as chromatography, recrystallization, and distillation.

Typical examples of the compound of formula (I) provided by the process of this invention are given below.

5-trifluoromethyldihydrouracil, 5-trifluoromethyldihydro-2-thiouracil,
1-methyl-5-trifluoromethyldihydrouracil,
1-methyl-5-trifluoromethyldihydro-2-thiouracil,
3-methyl-5-trifluoromethyldihydrouracil,
3-methyl-5-trifluoromethyldihydro-2-thiouracil,
1,3-dimethyl-5-trifluoromethyldihydrouracil,
1,3-dimethyl-5-trifluoromethyldihydro-2-thiouracil,
3-phenyl-5-trifluoromethyldihydrouracil,
3-phenyl-5-trifluoromethyldihydro-2-thiouracil,
3-benzyl-5-trifluoromethyldihydrouracil,
3-benzyl-5-trifluoromethyldihydro-2-thiouracil,
1-phenyl-5-trifluoromethyldihydrouracil,
1-phenyl-5-trifluoromethyldihydro-2-thiouracil,
1-benzyl-5-trifluoromethyldihydrouracil,
1-benzyl-5-trifluoromethyldihydro-2-thiouracil,
1-tetrahydrofuryl-5-trifluoromethyldihydrouracil,
1-tetrahydrofuryl-5-trifluoromethyldihydro-2-thiouracil,
3-tetrahydrofuryl-5-trifluoromethyldihydrouracil,
3-tetrahydrofuryl-5-trifluoromethyldihydro-2-thiouracil,
5-pentafluoroethyldihydrouracil,
5-pentafluoromethyldihydro-2-thiouracil,
3-methyl-5-pentafluoroethyldihydrouracil,
3-methyl-5-pentafluoroethyldihydro-2-thiouracil,
5-heptafluoropropyldihydrouracil,
5-heptafluoropropyldihydro-2-thiouracil,
5-nonafluorobutyldihydrouracil,
5-nonafluorobutyldihydro-2-thiouracil,
5-heptafluoro-iso-propyldihydrouracil,
5-heptafluoro-iso-propyldihydro-2-thiouracil,
5-nonafluoro-iso-butyldihydrouracil,
5-nonafluoro-iso-butyldihydro-2-thiouracil,
5-nonafluoro-sec-butyldihydrouracil,
5-nonafluoro-sec-butyldihydro-2-thiouracil,
5-nonafluoro-tert-butyldihydrouracil,
5-nonafluoro-tert-butyldihydro-2-thiouracil,
5-perfluorooctyldihydrouracil,
5-perfluorooctyldihydro-2-thiouracil,
3-tetrahydrofuryl-5-trifluoromethyldihydrouracil,
3-tetrahydrofuryl-5-trifluoromethyldihydro-2-thiouracil,
1,3-bis(tetrahydrofuryl)-5-pentafluoroethyldihydrouracil,
1,3-bis(tetrahydrofuryl)-5-Pentafluoroethyldihydro-2-thiouracil,
3-furyl-5-trifluoromethyldihydrouracil,
3-furyl-5-trifluoromethyldihydro-2-thiouracil,
3-(2,3,4,6-tetra-O-acetyl-β-D-glucopyranosyl)-5-trifluoromethyldihydrouracil,
3-(2,3,4,6-tetra-O-acetyl-β-D-glucopyranosyl)-5-trifluoromethyldihydro-2-thiouracil,
3-(3,5-di-o-benzoyl-2-deoxy-β-ribofuranosyl)-5-trifluoromethyldihydrouracil,
3-(3,5-di-o-benzoyl-2-deoxy-β-D-ribofuranosyl)-5-trifluoromethyldihydro-2-thiouracil,
3-(2,3,5-tri-o-benzoyl-β-D-ribofuranosyl)-5-trifluoromethyldihydrouracil, and
3-(2,3,5-tri-o-benzoyl-β-D-ribofuranosyl)-5-trifluoromethyldihydro-2-thiouracil.

Of the compounds of formula (I) produced by the process of this invention, a compound corresponding to formula (I) in which $R_f$ is trifluoromethyl and both $R^1$ and $R^2$ are hydrogen atoms, i.e. 5-trifluoromethyldihydrouracil, is an important intermediate for the production of trifluorothymidine and its derivatives having anticancer and antiviral activities. It can be converted to trifluorothymidine by the route schematically shown below (for details of the reaction, see C. Heidelberger, D. G. Parsons and D. C. Remy, J. Med, Chem., 7, 1(1964).

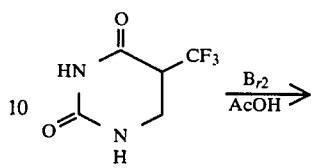

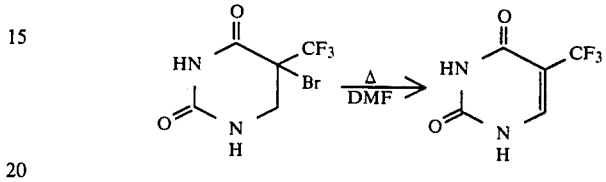

Some of the compounds of formula (I) produced by the process of this invention have antitumor activity as demonstrated by the following animal experiment, and may find utility as an anticancer agent.

Animal Experiment (1) Experimental animals

Inbred mice, $CDF_1$, C3H/Me, were purchased from Charles River Japan, Inc., and after feeding them for one week, five-week old male mice were used in the experiment (6 per group).

(2) Experimental tumor

Tumor cells ($1 \times 10^6$) of ascitic mastocarcinoma MM2 were transplanted into the abdominal cavity of each of $CDF_1$ and C3H/Me mice to give tumor bearing mice.

(3) Dosage and administration schedule

Each of the compounds produced in Examples 1 and 4 below (OF-1 to OF-3) was suspended in 0.5% CMC. The suspension was intraperitoneally administered to the mice in a dose of 50 mg/kg continuously (1 to 5 days) after transplantation of the tumor cells.

(4) Assessment

The antitumor effect was assessed from the rate of apothanasia (T/C %).

$$T/C \% = \frac{\text{Average number of days of survival of a test group}}{\text{Average number of days of survival of a control group}} \times 100$$

(5) Experimental results

The antitumor effects of the compounds tested on mouse ascitic mastocarcinoma MM2 are shown in Table 2. The average number of days of survival of the control group was 16.5±0.4 days. As a result of administering 50 mg/kg of OF-1, OF-2 and OF-3, an apothanasia rate of about 33 to about 52% was noted. With OF-1, OF-2 and OF-3, cases of complete cure were observed.

TABLE 1

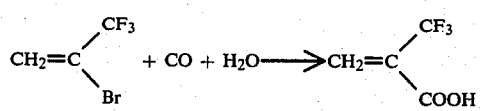

| Test compound | R¹ | R² | Dosage (mg/kg) | Rate of apothanasia(%) | Number of days of survival |
|---|---|---|---|---|---|
| OF-1 | CH₃ | CH₃ | 50 | 133 | >22 (1) survived out of 6; |
| OF-2 | CH₃ | H | 50 | >152 | >25 (2) survived out of 6; |
| OF-3 | H | CH₃ | 50 | >145 | >24 (4) survived out of 6 |
| Control | — | — | — | 100.0 | 16.5 ± 0.40 |

The following Referential Examples and Examples illustrate the present invention further.

REFERENTIAL EXAMPLE 1

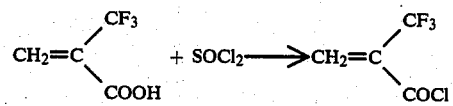

A mixture of dichlorobis(triphenylphosphine) palladium (5.5 g; 7.85×10⁻³ mole), 2-bromo-3,3,3-trifluoropropene (139 g; 0.794 mole), water (20 g; 1.11 moles) and triethylamine (109 g; 1.08 moles) in tetrahydrofuran (500 ml) was put in a one-liter stainless steel autoclave, and heated at 75° to 80° C. with stirring for 2 hours under a carbon monoxide pressure of 35 atmospheres. 2N-Hydrochloric acid was added to the reaction mixture, and the mixture was extracted with diethyl ether and then dried over anhydrous sodium sulfate. Distillation of the extract under reduced pressure gave 74.1 g (yield: 67%) of α-trifluoromethylacrylic acid having a boiling point of 90°/28 mmHg. m.p.: 52.5°–53.0° C.

¹H NMR (CDCl₃:TMS): δ6.52(q, J=1.3 Hz, 1H), 6.80 (q, J=1.8 Hz, 1H), 9.46 (s, 1H). ¹⁹F NMR (CDCl₃:CFCl₃): δ-66.5(bs).

IR (KBr): 3600–2400 ($\nu$O—H), 1710 ($\nu_{c=o}$), 1630 ($\nu_{c=c}$)cm⁻¹.

(Mass: m/e (rel. int): M⁺140 (67), 123 (40), 120 (12), 101 (26), 95 (26), 76 (73), 75 (56), 73 (13), 69 (100), 53 (11), 45 (54), 31 (17), 27 (12), 26 (14).

REFERENTIAL EXAMPLE 2

$$CH_2=C\begin{array}{c}CF_3\\COOH\end{array} + SOCl_2 \longrightarrow CH_2=C\begin{array}{c}CF_3\\COCl\end{array}$$

Thionyl chloride (11.5 ml; 158 mmoles) was added to α-trifluoromethylacrylic acid (19.7 g; 141 mmoles), and the mixture was heated under reflux for 22 hours. Distillation of the reaction mixture under atmospheric pressure gave 14.7 g (yield:66%) of α-trifluoromethylacryloyl chloride, B.p. 89°–90° C.

¹H NMR (CDCl₃:TMS): δ6.89(m, 1H), 7.06(m, 1H). ¹⁹F NMR (CDCl₃:CFCl₃): δ-65.9(bs).

REFERENTIAL EXAMPLE 3

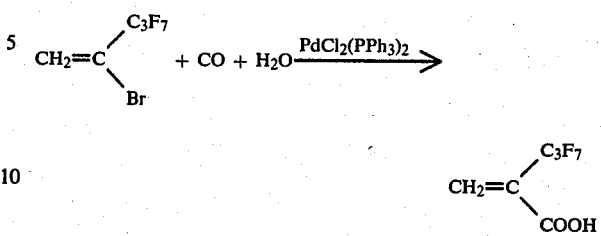

A mixture of dichlorobis(triphenylphosphine) palladium (35 mg; 0.05 mmole), 2-bromo-3,3,4,4,5,5,5-heptafluoro-1-pentene (1.48 g; 5 mmoles), triethylamine (1.4 m; 10 mmoles) and water (0.13 g; 7 mmoles) in tetrahydrofuran (5 ml) was put into a 50 ml stainless steel autoclave, and heated at 60° C. with stirring for 24 hours under a carbon monoxide pressure of 50 atmospheres. Dilute hydrochloric acid was added to the reaction mixture, and the mixture was extracted with diethyl ether and dried over anhydrous sodium sulfate. The solvent was evaporated, and the residue was subjected to preparative GLC to give 576 mg (yield:48%) of α-heptafluoropropylacrylic acid.

¹H NMR (CDCl₃:TMS): δ6.60(bs, 1H), 7.05 (t, J=2 Hz, 1H), 11.1 (bs, 1H). ¹⁹F NMR (CDCl₃:CFCl₃): δ-80.5 (t, J=10 Hz, 3F), −109.7(m, 2F), −124.4(bs, 2F).

IR(neat): 1725 cm⁻¹ ($\nu_{c=o}$), 1635 cm⁻¹ ($\nu_{c=c}$).

Mass: m/e (rel. int): M⁺240 (2), 101 (100).

Elemental analysis: C₆H₃F₇O₂:

|  | C(%) | H(%) |
|---|---|---|
| Calculated | 30.02 | 1.26 |
| Found | 30.09 | 1.29 |

EXAMPLE 1

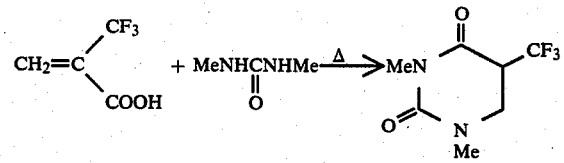

A mixture of α-trifluoromethylacrylic acid (700 mg; 5.0 mmoles) and 1,3-dimethylurea (441 mg; 5.0 mmoles) in dimethylformamide (DMF) (3 ml) was heated at 90° C. with stirring for 28 hours. DMF was evaporated under reduced pressure, and the residue was purified by a column chromatography on silicagel (chloroform) to give 861 mg (yield: 82%) of 1,3-dimethyl-5-trifluoromethyl-5,6-dihydrouracil (OF-1).

Mass spectrum: m/e (relative intensity) M⁺210 (93), 57 (100).

IR (neat): 1725, 1685 cm⁻¹ ($\nu_{c=o}$).

¹H NMR (CDCl₃:TMS): δ3.09 (s, 3H), 3.20 (s, 3H), 3.2–3.7(m, 3H). ¹⁹F NMR CDCl₃:CFCl₃): δ-67.9(m).

Elemental analysis for C₇H₉F₃N₂O₂: Calculated (%) C, 40.01; H, 4.32; N, 13.33. Found (%) C, 40.04; H, 4.20; N, 12.97.

EXAMPLE 2

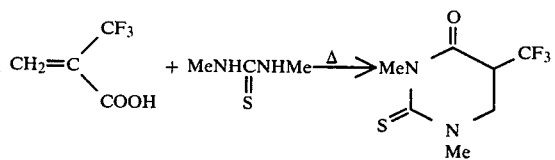

A mixture of α-trifluoromethylacrylic acid (700 mg; 5.0 mmoles) and 1,3-dimethylthiourea (552 mg; 5.3 mmoles) in DMF (3 ml) was heated at 90° C. with stirring for 28 hours. DMF was evaporated under reduced pressure, and the residue was purified by a column chromatography on silicagel (chloroform) to give 294 mg (yield: 26%) of 1,3-dimethyl-5-trifluoromethyl-5,6-dihydro-2-thiouracil.

Mass spectrum: m/e (relative intensity) M+226 (100), 129 (30), 74 (60), 73 (31), 42 (65).

IR (neat): 1710 cm$^{-1}$ ($\nu c=o$).

$^1$H NMR (CDCl$_3$:TMS): δ3.51 (s, 3H), 3.56(s, 3H), 3.4–3.7(m, 1H), 3.82 (bd, 2H). $^{19}$F NMR (CDCl$_3$:CFCl$_3$): δ-67.9 (d, J=8 Hz).

Elemental analysis for C$_7$H$_9$F$_3$N$_2$OS: Calculated (%): C, 37.17; H, 4.01; N, 12.38. Found (%): C, 37.42; H, 4.00; N, 12.38.

EXAMPLE 3

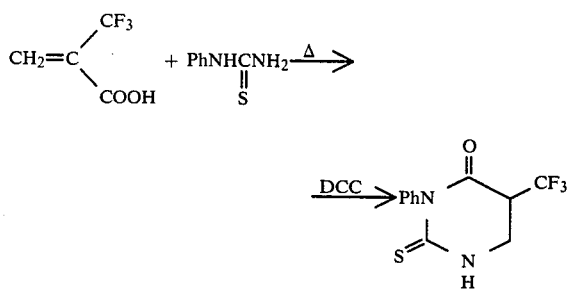

A mixture of α-trifluoromethylacrylic acid (700 mg; 5.0 mmoles) and phenylthiourea (780 mg; 5.1 mmoles) in DMF (5 ml) was heated at 90° C. with stirring for 8 hours. After cooling to 0° C., a solution of dicyclohexylcarbodiimide (DCC) (1.10 g; 5.3 mmoles) in 3 ml of DMF was added dropwise. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate:chloroform=1:3) to give 685 mg (yield: 50%) of 3-phenyl-5-trifluoromethyl-5,6-dihydro-2-thiouracil. m.p.: 185°–186.5° C.

Mass spectrum: m/e (relative intensity) M+274 (78), 273 (100).

IR (KBr): 3240, 3190, 3150 cm$^{-1}$ ($\nu$N—H), 1720 cm$^{-1}$ ($\nu c=o$).

$^1$H NMR (CDCl$_3$—CD$_3$OD:TMS): δ 3.5–4.0 (m, 1H), 3.98(bs, 1H), 4.0–4.3 (m, 2H), 6.8–7.7 (m, 5H). $^{19}$F NMR (CDCl$_3$—CD$_3$OD:CFCl$_3$): δ −67.3 (d, J=8 Hz).

Elemental analysis for C$_{11}$H$_9$F$_3$N$_2$OS: Calculated (%): C, 48.17; H, 3.31; N, 10.21. Found (%): C, 48.25; H, 3.04; N, 10.44.

EXAMPLE 4

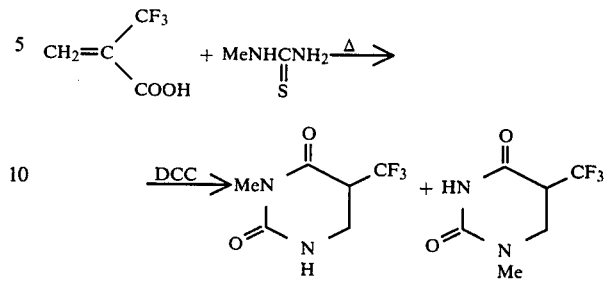

A mixture of α-trifluoromethylacrylic acid (700 mg; 5.0 mmoles) and methylurea (370 mg; 5.0 mmoles) in DMF (5 ml) was heated at 80° C. with stirring for 3 hours. After cooling to 0° C., a solution of dicyclohexylcarbodiimide (DCC) (1.05 g; 5.1 mmoles) in 3 ml of DMF was added dropwise. The mixture was stirred for 1 hour, and the precipitated solid was filtered off and washed with ethyl acetate. The solvent was evaporated under reduced pressure from the combined filtrates. The residue was purified by a column chromatography on silica gel (ethyl acetate:chloroform=1:3) to give 424 mg (yield: 43%) of 3-methyl-5-trifluoromethyl-5,6-dihydrouracil (OF-2) and 174 mg (yield: 18%) of 1-methyl-5-trifluoromethyl-5,6-dihydrouracil (OF-3).

3-Methyl-5-trifluoromethyl-5,6-dihydrouracil (OF-2): m.p.: 162°–163° C.

Mass spectrum: m/e (relative intensity) M+ 196 (100), 99 (50), 96 (46), 95 (32), 77 (35), 58 (66), 56 (54).

IR (KBr): 3260, 3140 cm$^{-1}$ ($\nu$N—H), 1730, 1705, 1690 cm$^{-1}$ ($\nu c=o$). $^1$H NMR (CD$_3$COCD$_3$:TMS): δ3.03(s, 3H), 3.4–4.0(m, 3H), 7.0(bs, 1H). $^{19}$F NMR (CD$_3$COCD$_3$:CFCl$_3$): δ-67.0(m).

Elemental analysis for C$_6$H$_7$F$_3$N$_2$O$_2$: Calculated (%): C, 36.74; H, 3.60; N, 14.28. Found (%): C, 36.43; H, 3.47; N, 14.16.

1-Methyl-5-trifluoromethyl-5,6-dihydrouracil (OF-3): M.p.: 142°–143° C.

Mass spectrum: m/e (relative intensity) M+ 196 (100), 77 (20), 57 (92), 56 (21), 44 (62), 43 (39), 42 (88).

IR (KBr): 3210, 3180 cm$^{-1}$ ($\nu$N—H), 1735, 1720, 1700 cm$^{-1}$ ($\nu c=o$).

$^1$H NMR (CD$_3$COCD$_3$:TMS): δ2.96(s, 3H), 3.4–4.0 (m, 3H), 9.4(bs, 1H). $^{19}$F NMR (CD$_3$COCD$_3$:CFCl$_3$): δ-67.0(m).

Elemental analysis for C$_6$H$_7$F$_3$N$_2$O$_2$: Calculated (%): C, 36.74; H, 3.60; N, 14.28. Found (%): C, 36.43; H, 3.41; N, 14.04.

EXAMPLE 5

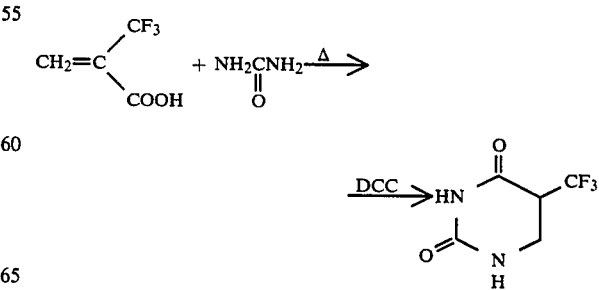

A mixture of α-trifluoromethylacrylic acid (700 mg; 5.0 mmoles) and urea (318 mg; 5.3 mmoles) in DMF (5 ml) was heated at 90° C. with stirring for 5 hours. After cooling to 0° C., a solution of DCC (1.09 g; 5.3 mmoles) in DMF (3 ml) was added dropwise. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate) to give 382 mg (yield: 42%) of 5-trifluoromethyl-5,6-dihydrouracil. m.p.: 203°–205° C. (dec.) [value reported in the literature 203°–205° C. (dec.)].

Mass spectrum: m/e (relative intensity) M+182 (100), 96 (66), 95 (60), 44 (47), 43 (75), 30 (53), 29 (44).

IR (KBr): 3230, 3120 cm⁻¹ ($\nu$N—H). 1750, 1710 cm⁻¹ ($\nu$c=o).

¹H NMR (CD₃COCD₃:TMS): δ3.4–4.2(m, 3H) 7.0(bs, 1H), 9.5(bs, 1H).

¹⁹F NMR (CD₃COCD₃:CFCl₃): δ-66.6(m).

EXAMPLE 6

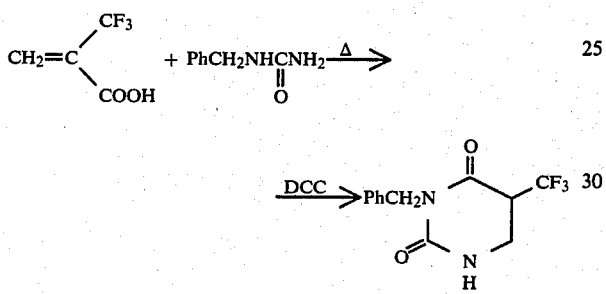

A mixture of α-trifluoromethylacrylic acid (700 mg; 5.0 mmoles) and benzylurea (796 mg; 5.3 mmoles) in DMF (5 ml) was heated at 90° C. with stirring for 5 hours. After the reaction mixture was cooled to 0° C., a solution of DCC (1.13 g; 5.5 mmoles) in DMF (3 ml) was added dropwise. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate:chloroform=1:1) to give 979 mg (yield: 72%) of 3-benzyl-5-trifluoromethyl-5,6-dihydrouracil. m.p.: 129.2°–129.7° C.

Mass spectrum: m/e (relative intensity) M+272 (100), 147 (56), 105 (58), 104 (99), 91 (97).

IR (KBr): 3260, 3140 cm⁻¹ ($\nu$N—H). 1735, 1690 cm⁻¹ ($\nu$c=o).

¹H NMR (CDCl₃:TMS): δ3.1–3.7(m, 3H), 4.94 (bs, 2H), 6.83 (bs, 1H), 7.1–7.5 (m, 5H). ¹⁹F NMR (CDCl₃:CFCl₃): −67.5 (m).

Elemental analysis for C₁₂H₁₁F₃N₂O₂: Calculated (%): C, 52.95; H, 4.07; N, 10.29. Found (%): C, 53.21; H, 3.94; N, 10.27.

EXAMPLE 7

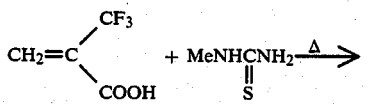

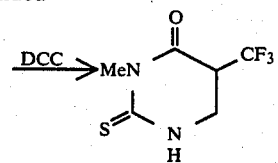

A mixture of α-trifluoromethylacrylic acid (700 mg; 5.0 mmoles) and methylthiourea (460 mg; 5.1 mmoles) in DMF (5 ml) was heated at 80° C. with stirring for 4 hours. After cooling to 0° C., a solution of DCC (1.09 g; 5.3 mmoles) in DMF (3 ml) was added dropwise to the reaction mixture. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate:chloroform=1:2) to give 572 mg (yield: 54%) of 3-methyl-5-trifluoromethyl-5,6-dihydro-2-thiouracil. m.p.: 137.5°–138° C.

Mass spectrum: m/e (relative intensity) M+212 (100), 56 (28), 43 (39), 42 (57).

IR (KBr): 3220, 3180, 3100 cm⁻¹ ($\nu$N—H). 1715, 1690 cm⁻¹ ($\nu$c=o).

¹H NMR (CD₃COCD₃:TMS): δ3.44(s, 3H), 3.7–4.3 (m, 3H), 10.1(bs, 1H). ¹⁹F NMR (CD₃COCD₃:CFCl₃): δ-67.1 (m).

Elemental analysis for C₆H₇F₂N₂OS: Calculated (%): C, 33.96; H, 3.33; N, 13.20. Found (%): C, 34.05; H, 3.24; N, 13.43.

EXAMPLE 8

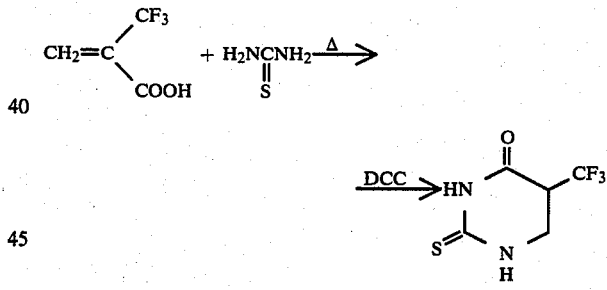

A mixture of α-trifluoromethylacrylic acid (700 mg; 5.0 mmoles) and thiourea (403 mg; 5.3 mmoles) in DMF (5 ml) was heated at 90° C. with stirring for 5 hours. After the reaction mixture was cooled to 0° C., a solution of DCC (1.05 g; 5.0 mmoles) in DMF (3 ml) was added dropwise. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate:chloroform=1:2) to give 536 mg (yield: 55%) of 5-trifluoromethyl-5,6-dihydro-2-thouracil. m.p.: 188.5°–190° C. (dec.)

Mass spectrum: m/e (relative intensity) M+198 (100), 69 (18), 60 (51), 59 (31), 43 (19), 42 (21).

IR (KBr): 3190, 3110 cm⁻¹ ($\nu$N—H). 1720 cm⁻¹ ($\nu$c=o).

¹H NMR (CDCl₃—CD₃OD:TMS): δ3.4–3.8(m. 3H), 3.96(bs, 2H). ¹⁹F NMR (CDCl₃—CD₃OD:CFCl₃): δ67.8(m).

Elemental analysis for C₅H₅F₃N₂OS: Calculated (%): C, 30.31; H, 2.54; N, 14.14. Found (%): C, 30.49; H, 2.21; N, 14.51.

EXAMPLE 9

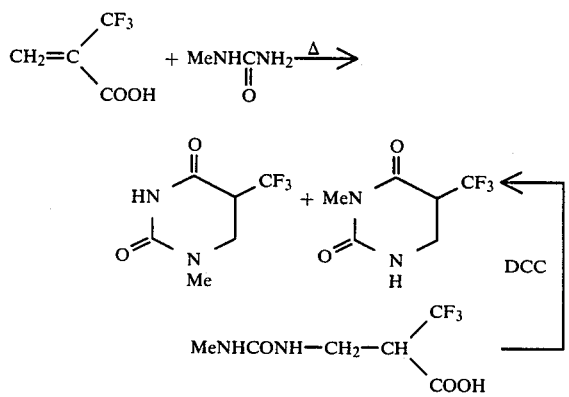

A mixture of α-trifluoromethylacrylic acid (700 mg; 5.0 mmoles) and methylurea (407 mg; 5.5 mmoles) in DMF (3 ml) was heated at 90° C. with stirring for 4 hours. DMF was evaporated under reduced pressure. The residue was purified by a column chromatography on silica gel to give 118 mg (yield 12%) of 1-methyl-5-trifluoromethyl-5,6-dihydrouracil (OF-3), 20 mg (yield: 2%) of 3-methyl-5-trifluoromethyl-5,6-dihydrouracil and 706 mg (yield: 66%) of 1-(2-hydroxycarbonyl-3,3,3-trifluoropropyl)-3-methylurea.

1-(2-Hydroxycarbonyl-3,3,3-trifluoropropyl)-3-methylurea: m.p.: 149.5°–150.5° C.

Mass spectrum: m/e (relative intensity) M+214(9), 30 (100).

IR (KBr): 3430, 3400 cm⁻¹ (νN—H), 3600–2200 cm⁻¹ (νO—H). 1740, 1725, 1610 cm⁻¹ (νc=o).

¹H NMR (CD₃COCD₃:TMS): δ2.70(s, 3H), 3.3–3.8(m, 3H), 5.9(bs, 1H). 6.1(bs, 1H), 10.7(bs, 1H). ¹⁹F NMR (CD₃COCD₃:CFCl₃): δ-66.1(m).

Elemental analysis for C₆H₉F₃N₂O₃: Calculated (%): C, 33.65; H, 4.24; N, 13.08. Found (%): C, 33.81; H, 4.06; N, 13.10.

A solution of DCC (428 mg; 2.1 mmoles) in DMF (1 ml) was added dropwise to a solution of 1-(2-hydroxycarbonyl-3,3,3-trifluoropropyl)-3-methylurea (428 mg; 2.0 mmoles) obtained above in DMF (2 ml). The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate:chloroform=1:1) to give 368 mg (yield: 94%) of 3-methyl-5-trifluoromethyl-5,6-dihydrouracil (OF-2).

EXAMPLE 10

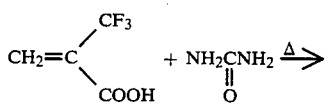

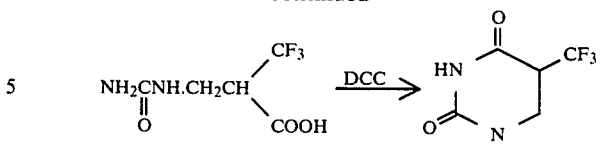

A mixture of α-trifluoromethylacrylic acid (700 mg; 5.0 mmoles) and urea (342 mg; 5.7 mmoles) in DMF (3 ml) was heated at 90° C. with stirring for 6 hours. DMF was evaporated under reduced pressure. The residue was purified by a column chromatography on silica gel (ethyl acetate) to give 540 mg (yield: 54%) of (2-hydroxycarbonyl-3,3,3-trifluoropropyl)urea. m.p.: 149°–149.5° C.

Mass spectrum: m/e (relative intensity) M+200 (1), 30 (100).

IR (KBr): 3480, 3410, 3370 cm⁻¹ (νN—H). 3700–2200 cm⁻¹ (νO—H). 1730, 1640 cm⁻¹ (νc=o).

¹H NMR (CD₃COCD₃:TMS): δ3.3–4.0(m, 3H), 5.3–7.0(m, 3H), 8.4(bs, 1H). ¹⁹F NMR (CD₃COCD₃:CFCl₃): δ-66.8(m).

A solution of 200 mg (1.0 mmole) of (2-hydroxycarbonyl-3,3,3-trifluoropropyl)urea obtained above in DMF (1 ml) was cooled to 0° C., and a solution of DCC (220 mg; 1.1 mmoles) in DMF (1 ml) was added dropwise. The mixture was stirred for 1 hour, and the precipitated solid was filtered off and washed with ethyl acetate. The solvents were evaporated under reduced pressure from the combined filtrates. The residue was purified by a column chromatography on silica gel (ethyl acetate) to give 116 mg (yield: 64%) of 5-trifluoromethyl-5,6-dihydrouracil.

EXAMPLE 11

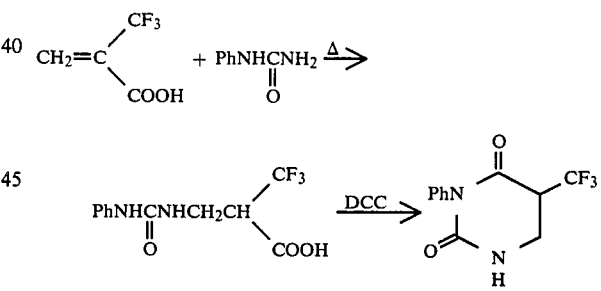

A mixture of α-trifluoromethylacrylic acid (700 mg; 5.0 mmoles) and phenylurea (776 mg; 5.7 mmoles) in DMF (5 ml) was heated at 90° C. with stirring for 8 hours. DMF was evaporated under reduced pressure, and the residue was purified by a column chromatography on silica gel (ethyl acetate) to give 1.09 g (yield: 79%) of 1-(2-hydroxycarbonyl-3,3,3-trifluoropropyl)-3-phenylurea. m.p.: 180.5°–181° C.

Mass spectrum: m/e (relative intensity) M+276 (5), 93 (100).

IR (KBr): 3350 cm⁻¹ (νN—H). 3700–2300 cm⁻¹ (νO—H). 1735, 1600 cm⁻¹ (νc=o).

¹HNMR (CD₃COCD₃:TMS): δ3.3–4.0(m, 3H), 6.1(bs, 1H), 6.7–7.6(m, 5H), 7.8(bs, 1H), 8.1(bs, 1H). ¹⁹F NMR (CD₃COCD₃:CFCl₃): δ-66.6(m).

Elemental analysis for C₁₁H₁₁F₃N₂O₃: Calculated (%): C, 47.83; H, 4.01; N, 10.14. Found (%): C, 47.70; H, 3.65; N, 9.81.

A solution of DCC (206 mg; 1.0 mmole) in DMF (0.5 ml) was added dropwise to a solution of 1-(2-hydroxycarbonyl-3,3,3-trifluoropropyl)-3-phenylurea (276 mg; 1.0 mmole) obtained above in DMF (1 ml), and the mixture was stirred for 1 hour. The precipitated solid was filtered off, and washed with ethyl acetate. The solvents were evaporated under reduced pressure from the combined filtrates. The residue was purified by a column chromatography on silica gel (ethyl acetate:chloroform=1:3) to give 120 mg (yield: 47%) of 3-phenyl-5-trifluoromethyl-5,6-dihydrouracil. m.p.: 215°–216° C.

Mass spectrum: m/e (relative intensity) M+258(73), 93 (100).

IR (KBr): 3240, 3130 cm$^{-1}$ ($\nu$N—H). 1740, 1695 cm$^{-1}$ ($\nu$c=o).

$^1$H NMR (CD$_3$COCD$_3$:TMS): δ3.6–4.2(m. 3H), 7.0–7.5(m, 6H). $^{19}$F NMR (CD$_3$COCD$_3$:CFCl$_3$): δ-66.5(d, J=8 Hz).

Elemental analysis for C$_{11}$H$_9$F$_3$N$_2$O$_2$: Calculated (%): C, 51.17; H, 3.51; N, 10.85. Found (%): C, 51.35; H, 3.71; N, 10.87.

EXAMPLE 11

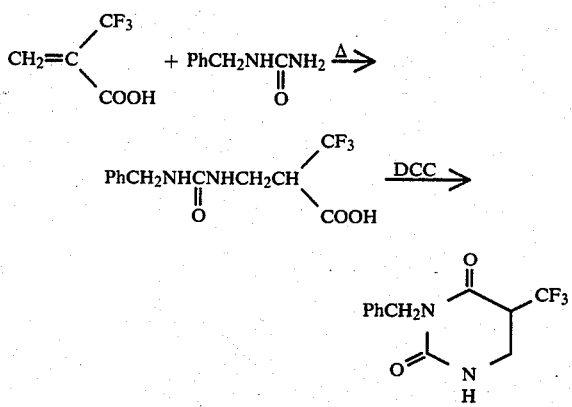

A mixture of α-trifluoromethylacrylic acid (700 mg; 5.0 mmole) and benzylurea (841 mg; 5.6 mmoles) in DMF (3 ml) was heated at 90° C. with stirring for 28 hours. DMF was evaporated under reduced pressure, and the residue was recrystallized from ethyl acetate-chloroform to give 1.10 g (yield: 76%) of 1-benzyl-3-(2-hydroxycarbonyl-3,3,3-trifluoropropyl)urea. m.p.: 183°–183.5° C.

Mass spectrum: m/e (relative intensity) M+290(18), 106 (100).

IR (KBr): 3390 cm$^{-1}$ ($\nu$N—H). 3700–2300 cm$^{-1}$ ($\nu$O—H). 1740, 1600 cm$^{-1}$ ($\nu$c=o).

$^1$H NMR (CD$_3$COCD$_3$:TMS): δ3.4–3.9(m, 3H), 4.30(m, 2H), 6.15(bd, 2H), 7.27(m, 6H). $^{19}$F NMR (CD$_3$COCD$_3$:CFCl$_3$): δ-66.8 (m).

Elemental analysis for C$_{12}$H$_{13}$F$_3$N$_2$O$_3$: Calculated (%) C, 49.66; H, 4.51; N, 9.65. Found (%): C, 49.43; H, 4.55; N, 9.88.

A solution of DCC (430 mg; 2.1 mmoles) in DMF (1 ml) was added dropwise to a solution of 1-benzyl-3-(2-hydroxycarbonyl-3,3,3-trifluoropropyl)urea (580 mg; 2.0 mmoles) obtained above in DMF (2 ml). One hour later, the precipitated solid was filtered off and washed with ethyl acetate. The solvents were evaporated under reduced pressure from the combined filtrates. The residue was purified by a column chromatography on silica gel (ethyl acetate:chloroform=1:1) to give 468 mg (yield: 86%) of 3-benzyl-5-trifluoromethyl-5,6-dihydrouracil.

EXAMPLE 13

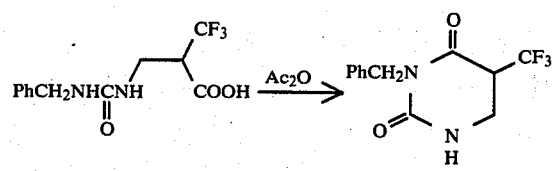

Acetic anhydride (5 ml) was added to 290 mg (1.0 mmole) of 1-benzyl-3-(2-hydroxycarbonyl-3,3,3-trifluoropropyl)urea synthesized in Example 12, and the mixture was heated under reflux for 30 minutes. The solvent was evaporated under reduced pressure. The residue was purified by a column chromatography on silica gel (ethyl acetate:chloroform=1:1) to give 176 mg (yield: 65%) of 3-benzyl-5-trifluoromethyl-5,6-dihydrouracil.

EXAMPLE 14

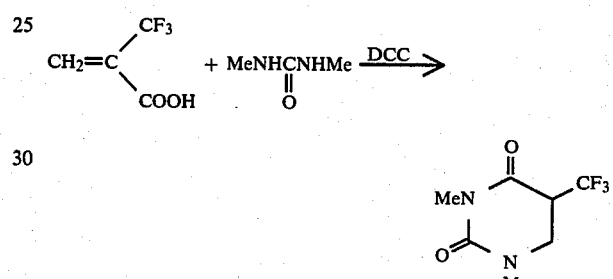

A mixture of α-trifluoromethylacrylic acid (700 mg; 5.0 mmoles) and 1,3-dimethylurea (419 mg; 4.8 mmoles) in DMF (5 ml) was cooled to 0° C., and then a solution of DCC (1.21 g; 5.9 mmoles) in DMF (3 ml) was added dropwise. The mixture was stirred at 0° C. for 1 hour. The precipitated solid was filtered off, and washed with ethyl acetate. The solvents were evaporated under reduced pressure from the combined filtrates. The residue was purified by a column chromatography on silica gel to give 566 mg (yield 57%) of 1,3-dimethyl-5-trifluoromethyl-5,6-dihydrouracil (OF-1).

EXAMPLE 15

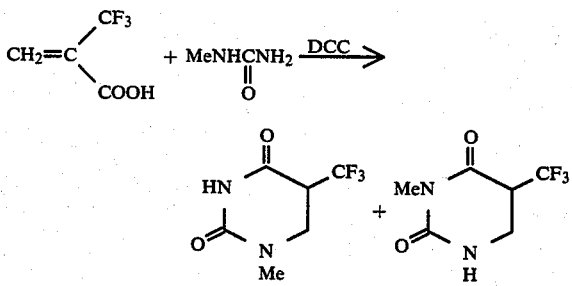

A mixture of α-trifluoromethylacrylic acid (700 mg; 5.0 mmoles) and methylurea (378 mg; 5.1 mmoles) in DMF (5 ml) was cooled to 0° C., and a solution of DCC (1.07 g; 5.2 mmoles) in DMF (3 ml) was added dropwise. The mixture was stirred for 1 hour, and the precipitated solid was filtered off and washed with ethyl acetate. DMF was evaporated under reduced pressure from the combined filtrates. The residue was purified by a column chromatography on silica gel (ethyl acetate:chloroform=1:3) to give 420 mg (yield: 43%) of 1-methyl-5-trifluoromethyl-5,6-dihydrouracil (OF-3) and 30 mg (yield: 15%) of 3-methyl-5-trifluoromethyl-5,6-dihydrouracil (OF-2).

EXAMPLE 16

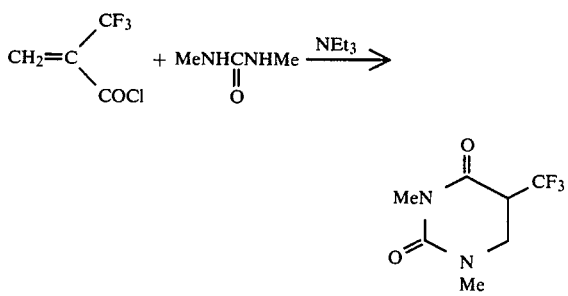

A solution of 1,3-dimethylurea (168 mg; 1.9 mmoles) in DMF (2 ml) was cooled to 0° C., and α-trifluoromethylacryloyl chloride (317 mg; 2.0 mmoles) and triethylamine (0.31 ml; 2.2 mmoles) were added dropwise. The mixture was stirred at 0° C. for 2 hours, and then water (20 ml) was added. The mixture was extracted with methylene chloride (20 ml×1, 10 ml×2). The combined extracts were dried over anhydrous magnesium sulfate, filtered and concentrated under reduced pressure. The residue was purified by a column chromatography on silica gel (chloroform) to give 197 mg (yield: 49%) of 1,3-dimethyl-5-trifluoromethyl-5,6-dihydrouracil.

EXAMPLE 7

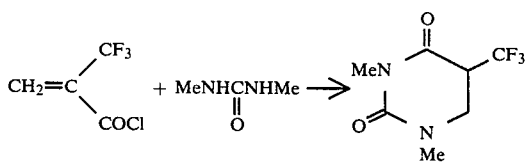

A solution of 1,3-dimethylurea (423 mg; 4.8 mmoles) in DMF (5 ml) was cooled to 0° C., and α-trifluoromethylacryloyl chloride (792 mg; 5.0 mmoles) was added dropwise. The mixture was stirred at room temperature for 1 hour. Then, water (20 ml) was added, and the mixture was extracted with methylene chloride (20 ml×1, 10 ml×2). The combined extracts were dried over anhhdrous magnesium sulfate, filtered, and concentrated under reduced pressure. The residue was purified by a column chromatography on silica gel (chloroform) to give 508 mg (yield: 50%) of 1,3-dimethyl-5-trifluoromethyl-5,6-dihydrouracil (OF-1).

EXAMPLE 18

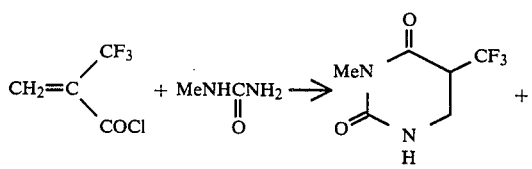

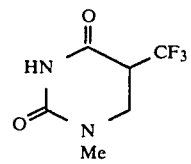

A solution of methylurea (148 mg; 2.0 mmoles) in DMF (2 ml) was cooled to 0° C., and α-trifluoromethylacryloyl chloride (317 mg; 2.0 mmoles) was added dropwise. The mixture was stirred at room temperature for 1 hour, and water (20 ml) was added. The mixture was extracted with methylene chloride (20 ml×1, 10 ml×2). The combined extracts were dried over anhydrous magnesium sulfate, filtered, and concentrated under reduced pressure. The residue was purified by a column chromatography on silica gel (chloroform:ethyl acetate=3:1) to give 39 mg (yield: 10%) of 1-methyl-5-trifluoromethyl-5,6-dihydrouracil (OF-3) and 117 mg (yield: 30%) of 3-methyl-5-trifluoromethyl-5,6-dihydrouracil (OF-2).

EXAMPLE 19

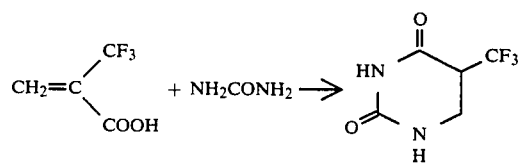

A mixture of α-trifluoromethylacrylic acid (700 mg; 5 mmoles), urea (300 mg; 5 mmoles) and acetic anhydride (2 ml) was heated at 100° C. with stirring for 1 hour. After cooling to 0° C., the precipitated solid was filtered off to give 450 mg (yield: 40%) of 5-trifluoromethyl-5,6-dihydrouracil. The solvent was evaporated under reduced pressure from the filtrate, and the residue was recrystallized from ethanol to give additional 160 mg (yield: 27%) of 5-trifluoromethyl-5,6-dihydrouracil. The total yield of the product was 67%.

The physical and spectral properties of the resulting 5-trifluoromethyl-5,6-dihydrouracil completely agreed with those of the product obtained in Example 5.

EXAMPLE 20

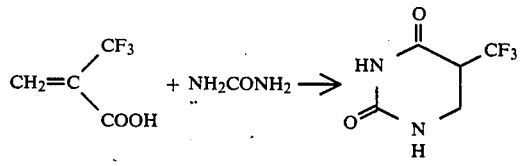

A mixture of α-trifluoromethylacrylic acid (350 mg; 2.5 mmoles), urea (162 mg; 2.7 mmoles) and acetic anhydride (2 ml) was heated at 80° C. with stirring for 2 hours. After cooling to 0° C., the precipitated white solid was filtered off to give 210 mg (yield: 46%) of 5-trifluoromethyldihydrouracil. The solvent was evaporated under reduced pressure from the filtrate. The residue was crystallized from ethanol to give additional 95 mg (yield: 21%) of the above product. The total yield was 67%.

EXAMPLE 21

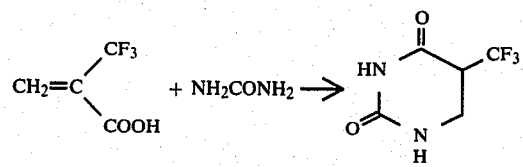

A mixture of α-trifluoromethylacrylic acid (350 mg; 2.5 mmoles), urea (170 mg: 2.8 mmoles) and acetic anhydride (1 ml) in dimethyl-formamide (2 ml) was stirred at 100° C. for 40 minutes. The solvent was evaporated under reduced pressure, and the residue was recrystallized from ethanol to give 290 mg (yield: 64%) of 5-trifluoromethyldihydrouracil.

EXAMPLE 22

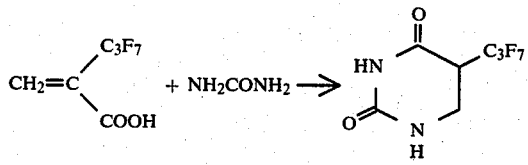

A mixture of α-heptafluoropropylacrylic acid (240 mg; 1.0 mmole), urea ( 64 mg; 1.1 mmoles) and acetic anhydride (0.6 ml) was heated at 100° C. with stirring for 40 minutes. Then, ethanol (3 ml) was added to the reaction mixture to give 180 mg (yield: 64%) of 5-heptafluoropropyldihydrouracil as colorless crystals. m.p.: 223°-224 (decomp.).

$^1$H NMR (CD$_3$COCD$_3$—CD$_3$SOCD$_3$:TMS): δ3.3–4.2 (m, 3H), 7.6(bs, 1H), 10.4 (bs, 1H). $^{19}$F NMR (CD$_3$COCD$_3$—CD$_3$SOCD$_3$:CFCl$_3$): δ79.7 (t, J=10 Hz, 3F), 111.2(m, 2F), 123.2(bd, J=7 Hz, 2F).

IR (KBr): 3250, 3140 cm$^{-1}$ ($\nu$N—H), 1760, 1710 cm$^{-1}$ ($\nu$c=o).

Mass: m/e (refl. int.): M+282 (18), 99 (100).

Elemental analysis for C$_7$H$_5$F$_7$N$_2$O$_2$

|  | C (%) | H (%) | N (%) |
|---|---|---|---|
| Calculated: | 29.80 | 1.79 | 9.93 |
| Found: | 30.03 | 1.84 | 9.88 |

EXAMPLE 23

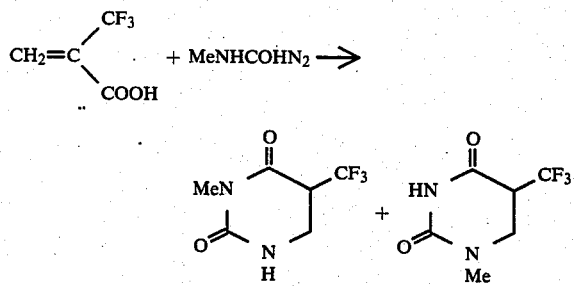

A mixture of α-trifluoromethylacrylic acid (350 mg; 2.5 mmoles), methylurea (193 mg; 2.6 mmoles) and acetic anhydride (2 ml) was heated with stirring at 100° C. for 1 hour, and the solvent was evaporated under reduced pressure. The residue was recrystallized from chloroform-hexane to give 392 mg (yield 80%) of a 2:3 mixture of 1-methyl-5-trifluoromethyldihydrouracil (OF-3) and 3-methyl-5-trifluoromethyldihydrouracil (OF-2) as in Example 4.

The isomers were separated from each other by a column chromatography on silica gel (ethyl acetate:chloroform=1:3).

EXAMPLE 24

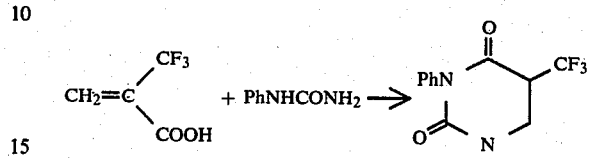

A mixture of α-trifluoromethylacrylic acid (350 mg; 2.5 mmoles), phenylurea (353 mg; 2.6 mmoles) and acetic anhydride (2 ml) was heated at 100° C. with stirring for 1 hour. After cooling, the precipitated solid was collected by filtration to give 298 mg (yield: 46%) of 3-phenyl-5-trifluoromethyldihydrouracil. The solvent was evaporated from the filtrate, and the residue was recrystallized from chloroform/hexane to give additional 133 mg (yield: 21%) of the above product. The total yield was 67%. The physical and spectral properties of the resulting 3-phenyl-5-trifluoromethyldihydrouracil completely agreed with those of the product obtained in Example 11.

EXAMPLE 25

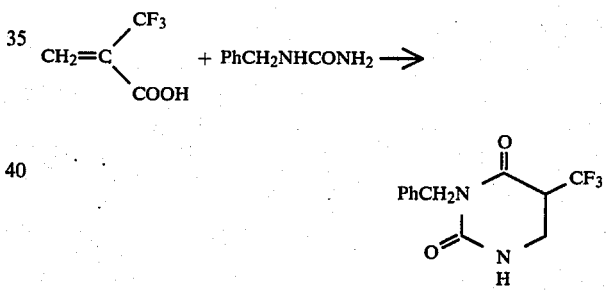

A mixture of α-trifluoromethylacrylic acid (350 mg; 2.5 mmoles), benzylurea (389 mg; 2.6 mmoles) and acetic anhydride (2 ml) was heated with stirring at 100° C. for 1 hour. The solvent was evaporated under reduced pressure, and the residue was recrystallized from chloroform/hexane to give 500 mg (yield: 72%) of 3-benzyl-5-trifluoromethyldihydrouracil. The physical and spectral properties of this product completely agreed with those of the product obtained in Example 6.

EXAMPLE 26

A mixture of α-trifluoromethylacrylic acid (4.31 g; 30.8 mmoles), 1,3-dimethylurea (2.75 g; 31.2 mmoles) and acetic anhydride (17 ml) was heated at 100° C. with stirring for one hour. The solvent was evaporated under reduced pressure, and the residue was purified by a column chromatography on silica gel (CHCl$_3$) to give 5.50 g (yield: 84%) of 1,3-dimethyl-5-trifluoromethyldihydrouracil.

What we claim is:

1. A process for preparing a 5-perfluoroalkyldihydrouracil compound of the formula

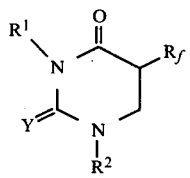

wherein $R_f$ represents a perfluoroalkyl group having 1 to 5 carbon atoms, each of $R^1$ and $R^2$ represents a hydrogen atom, or an alkyl group having 1 to 5 carbon atoms, and Y is an oxygen atom, which comprises:
reacting a compound of the formula

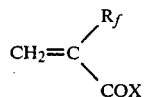

wherein X represents a halogen atom or a hydroxyl group, and $R_f$ is as defined above,
with a urea compound of the formula

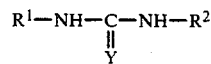

wherein $R^1$, $R^2$ and Y are as defined above, provided that when X is a hydroxyl group and at least one of $R^1$ and $R^2$ is a hydrogen atom, said reaction is carried out in the presence of a condensing agent.

2. The process of claim 1, wherein the condensing agent is dicyclohexyl carbodiimide, polyphosphoric acid, p-toluene-sulfonic acid or a carboxylic acid anhydride.

3. The process of claim 2 wherein the condensing agent is dicyclohexyl carbodiimide or acetic anhydride.

4. The process of claim 1, wherein when X is a hydroxyl group and at least one of $R^1$ and $R^2$ is a hydrogen atom, the reaction is carried out in the presence of a condensing agent at a temperature of $-20°$ C. to $120°$ C.

5. The process of claim 1, wherein when X is a hydroxyl group and both $R^1$ and $R^2$ represent a substituent other than a hydrogen atom, the reaction is carried out at a temperature of $50°$ C. to $200°$ C.

6. The process of claim 1, wherein when X is a halogen atom, the reaction is carried out at a temperature of $-20°$ C. to $50°$ C.

7. A process for preparing a 5-perfluoroalkyldihydrouracil compound of the formula wherein $R_f$ represents a perfluoroalkyl group having 1 to 5 carbon atoms, each of $R^1$ and $R^2$ represents a hydrogen atom or an alkyl group having 1 to 5 carbon atoms and Y is an oxygen atom
which comprises:
cyclizing a compound of the formula

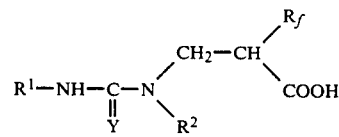

wherein $R_f$, $R^1$, $R^2$ and Y are as defined above in the presence of a condensing agent selected from the group consisting of dicyclohexylcarbodiimide (DCC), polyphosphoric acid, p-toluenesulfonic acid, and carboxylic acid anhydrides of the formula $(R^3CO)_2O$ wherein $R^3$ represents a hydrogen atom, a lower alkyl group, a lower haloalkyl group or phenyl, or the two $R^3$'s may together form a lower alkylene group.

8. The process of claim 7 wherein the condensing agent is dicyclohexyl carbodiimide or acetic anhydride.

9. The process of claim 7, wherein the cyclization is carried out at a temperature of $-20°$ C. to $200°$ C.

10. A compound of the formula

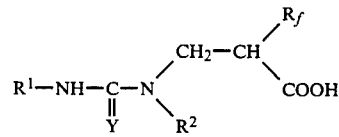

wherein $R_f$ represents a perfluoroalkyl group having 1 to 5 carbon atoms, each of $R^1$ and $R^2$ represents a hydrogen atom or an alkyl group having 1 to 5 carbon atoms, and Y represents an oxygen atom.

11. The compound of claim 10 wherein $R_f$ is a trifluoromethyl group.

12. The compound of claim 10 wherein each of $R^1$ and $R^2$ represents a hydrogen atom or a methyl group.

* * * * *